US006166191A

United States Patent [19]
Randazzo

[11] Patent Number: 6,166,191
[45] Date of Patent: *Dec. 26, 2000

[54] HUMAN POLYHOMEOTIC 1(HPH1) ACTS AS AN ONCOGENE

[75] Inventor: Filippo M. Randazzo, Emeryville, Calif.

[73] Assignee: Chiron Corporation, Emeryville, Calif.

[*] Notice: This patent is subject to a terminal disclaimer.

[21] Appl. No.: 08/916,352

[22] Filed: Aug. 22, 1997

Related U.S. Application Data

[60] Provisional application No. 60/024,349, Aug. 23, 1996, provisional application No. 60/031,569, Dec. 4, 1996, and provisional application No. 60/036,939, Feb. 6, 1997.

[51] Int. Cl.[7] .......................... C12N 15/11; C12N 15/63; C12N 1/21; C07H 21/04
[52] U.S. Cl. .................. 536/23.5; 536/23.1; 536/24.31; 435/320.1; 435/252.3
[58] Field of Search ................................ 536/23.1, 23.5, 536/24.31; 435/325, 320.1, 252.3

[56] References Cited

FOREIGN PATENT DOCUMENTS

WO 95/31560  11/1995  WIPO.

OTHER PUBLICATIONS

Sato et al., "Homoeosis in Drisophila: A New Enhancer of Polycomb and Related Homoeotic Mutations" *Genetics* 105:357–370, Oct., 1983.

Kennison and Tamkun, "Dosage–Dependent Modifiers of Polycomb and Antennapedia Mutations in Drosophila" *Proc. Natl. Acad. Sci. USA* 85:8136–8140, Nov., 1988.

Lewin, "Commitment and Activation at Pol II Promoters: A Tail of Protein—Protein Interactions" *Cell* 61:1161–1164, Jun., 1990.

Paro, "Imprinting a Determined State into the Chromatin of Drosophila" *TIG* 6(20):416–421, Dec., 1990.

Goebl, "The Bmi–1 and mel–18 Gene Products Define a New Family of DNA–Binding Proteins Involved in cell Proliferation and Tumorigenesis" *Cell* 66:623, Aug., 1991.

Brunk et al., "Drosophila Genes Posterior Sex Combs and Suppressor Two of Zeste Encode Proteins With Homology to the Murine bmi–1 Oncogene" *Nature* 353:351–353, Sep., 1991.

van Lohuizen et al., "Sequence Similarity Between the Mammalian bmi–1 Proto–Oncogene and the Drosophila Regulatory Genes Psc and Su(z)2" *Nature* 353:353–355, Sep., 1991.

DeCamillis et al., "The Polyhomeotic Gene of Drosophila Encodes a Chromatin Protein that Shares Polytene Chromosome–Binding Sites with Polycomb" *Genes and Development* 6:223–232, 1992.

Felsenfeld, "Chromatin as an Essential Part of the Transcriptional Mechanism" *Nature* 355:219–224, Jan., 1992.

Sinclair et al., "Genetic Analysis of the Additional Sex Combs Locus of *Drosophila Melanogaster*" *Genetics* 130:817–825, Apr., 1992.

Travers, "The Reprogramming of Transcriptional Competence" *Cell* 69:573–575, May, 1992.

Djabali et al., "A Trithorax–Like Gene is Interrupted by Chromosome 11q23 Translocations in Acute Leukaemias" *Nature Genetics* 2:113–118, Oct., 1992.

Gu et al., "The t(4;11) Chromosome Translocation of Human Acute Leukemias Fuses the ALL–1 Gene, Related to Drosophila trithorax, to the AF–4 Gene" *Cell* 71:701–708, Nov., 1992.

Tkachuk et al., "Involvement of a Homolog of *Drosophila Trithorax* by 11q23 Chromosomal Translations in Acute Leukemias" *Cell* 71:691–700, Nov., 1992.

Winston and Carlson, "Yeast SNF/SWI Transcriptional Activators and the SPT/SIN Chromatin Connection" *TIG* 8(11):387–391, Nov., 1992.

Barba et al., "Hox Gene Expression in Human Cancers" *Advances in Nutrition and Cancer*, Zappia et al., Eds., Plenum Press, N.Y., pp. 45–47, 1993.

Cillo, "Hox Genes in Human Cancers" *Invasion Metastasis* 14:38–49, 1994–1995.

Moehrle and Paro, "Spreading the Silence: Epigenetic Transcriptional Regulation During Drosophila Development" *Developmental Genetics* 15:478–484, 1994.

Kennison, "Transcriptional Activation of Drosophila Homeotic Genes from Distant Regulatory Elements" *TIG* 9(3):75–79, Mar., 1993.

van der Lugt et al., "Posterior Transformation, Neurological Abnormalities, and Severe Hematopoietic Defects in Mice with a Targeted Deletion of the bmi–1 proto–oncogene" *Genes and Development* 8:757–769, 1994.

Denis and Green, "A Novel, Mitogen–Activated Nuclear Kinase is Related to a Drosophila Developmental Regulator" *Genes and Development* 10:261–271, 1996.

Epstein, "Polycomb and Friends" *BioEssays* 14(6):411–413, 1992.

Chiba et al., "Two Human Homologues of *Saccharomyces cerevisiae* SW12/SNF2 and *Drosophila brahma* are Transcriptional Coactivators Cooperating with the Estrogen Receptor and the Retinoic Acid Receptor" *Nucleic Acids Research* 22(10):1815–1820, 1994.

Nomura et al., "Isolation and Characterization of Retinoic Acid–Inducible cDNA Clones in F9 Cells: One of the Early Inducible Clones Encodes a Novel Protein Sharing Several Highly Homologous Regions with a *Drosophila polyhomeotic* Protein" *Differentiation* 57:39–50, 1994.

Watson et al., "Drisophila in Cancer Research: the First Fifty Tumor Suppressor Genes" *J. Cell Science* 18:19–33, 1994.

Kanno et al., "mel–18, a Polycomb Group–Related Mammalian Gene, Encodes a Transcriptional Negative Regulator With Tumor Suppressive Activity" *The EMBO Journal* 14(22):5672–5678, 1995.

(List continued on next page.)

*Primary Examiner*—Nancy A. Johnson
*Attorney, Agent, or Firm*—Jane E. R. Potter; Kimberlin L. Morley; Robert P. Blackburn

[57] ABSTRACT

A novel human oncogene termed polyhomeotic 1 is disclosed. The human polyhomeotic 1 gene and protein can be used, inter alia, as a diagnostic tool for neoplastic disorders. The gene can also be used to identify a p13 region of human chromosome 12.

12 Claims, 1 Drawing Sheet

OTHER PUBLICATIONS

Santamaria and Randsholt, "Characterization of a Region of the X Chromosome of Drosophila Including multi sex combs (mxc), a Polycomb Group Gene which also Functions as a Tumour Suppressor" *Mol. Gen. Genet. 246*:282–290, 1995.

Pirrotta, "Chromatin Complexes Regulating Gene Expression in Drosophila" *Current Opinion in Genetics and Development 5*:466–472, 1995.

Stuart et al., "PAX and HOX in Neoplasia" *Advances in Genetics 33*:255–274, 1995.

Tamkun, "The Role of Brahma and Related Proteins in Transcription and Development" *Current Opinion in Genetics and Development 5*:473–477, 1995.

Yu et al., "Altered Hox Expression and Segmental Identity in MII–mutant Mice" *Nature 378*:505–508, Nov., 1995.

Gunster et al., "Identification and Characterization of Interactions Between the Vertebrate Polycomb–Group Protein BMI1 and Human Homologs of Polyhomeotic" *Molecular and Cellular Biology 17*(4) :2326–2335, Apr., 1997.

Hillier et al., "The WashU–Werck EST Project" May 10, 1995 (abstract) (Database EMBL EMEST2, Release 44) ACC #R77179 ID HS 179144.

Pujana et al., "Cloning (CAG/GTC)n STSs by an Alu–(CAG.GTC)n PCR Method: an Approach to Human Chromosome 12 and Spinocerebellar Ataxia 2 (SCA2)" *Nucleic Acids Research 24*(18):3651–3652. 1996.

Chepelinsk et al., "Major Intrinsic Protein Gene Prod.—Used to Detect Cataracts and DNA Encoding it Used as probe for Human Genome" Feb. 25, 1992 (abstract) (Database WPI–13 Derwent).

Pujana et al., "Cloning (CAG.GTC)n STSs by an Alu–(CAG/GTC)n PCR Method: an Approach to Human Chromosome 12 and Spinocerebellar Ataxia 2 (SCA2)" May 27, 1996 (Database EMBL EMSTS, Release 47) Acc # X97939 ID HSSTS91BP Sambrook, Molecular Cloning: A Laboratory Manual, 2 ed. 1989 p. 11.55–57, 11.47.

Alkema, EMBL/GeneBank Database Aug. 15, 1996 Accession U63386 NID g 1490545.

EMBL/Genbank Accession No N41621 (91165652) Jun. 24, '96.

EMBL/Genebank Accession No. T52018 (g653878) Feb. 8, '95.

EMBL/Genebank Accession No. R16168 (g768096) Apr. 13, '95.

FIG. 1 hph2 Expression

HUMAN POLYHOMEOTIC 1(HPH1) ACTS AS AN ONCOGENE

This application claims the benefit of the following copending U.S. provisional applications: Ser. No. 60/024,349, filed Aug. 23, 1996, Ser. No. 60/031,569, filed Dec. 4, 1996, and Ser. No. 60/036,939, filed Feb. 6, 1997, each of which is incorporated by reference herein.

TECHNICAL AREA OF THE INVENTION

The invention relates to the area of oncogenesis. More particularly, the invention relates to oncogenes and proteins.

BACKGROUND OF THE INVENTION

Mutations in oncogenes play an important role in the development of neoplasias. Detection of mutations in oncogenes can be used to detect neoplastic cells and genetic predispositions to neoplasias. Thus, there is a need in the art for the identification of mammalian oncogenes which can be used in methods of diagnosing, prognosing, and treating neoplastic cells in humans and other mammals.

SUMMARY OF THE INVENTION

It is an object of the invention to provide an isolated and purified human polyhomeotic 1 protein.

It is another object of the invention to provide an isolated and purified human polyhomeotic 1 polypeptide.

It is yet another object of the invention to provide an hph1 fusion protein.

It is still another object of the invention to provide a preparation of antibodies.

It is yet another object of the invention to provide an isolated and purified subgenomic polynucleotide.

It is still another object of the invention to provide an expression construct for expressing all or a portion of a human polyhomeotic 1 protein.

It is a further object of the invention to provide a homologously recombinant cell comprising a DNA construct.

It is even another object of the invention to provide a method of identifying neoplastic tissue of a human.

It is another object of the invention to provide a method to aid in the diagnosis or prognosis of neoplasia in a human.

It is yet another object of the invention to provide a method to aid in detecting a genetic predisposition to neoplasia in a human.

It is still another object of the invention to provide a method of identifying a human chromosome 12.

It is still another object of the invention to provide a method of inducing a cell to de-differentiate.

These and other objects of the invention are provided by one or more of the embodiments described below.

One embodiment of the invention provides an isolated and purified human polyhomeotic 1 protein. The isolated and purified human polyhomeotic 1 has the amino acid sequence shown in SEQ ID NO:2.

Another embodiment of the invention provides an isolated and purified human polyhomeotic 1 polypeptide. The isolated and purified human polyhomeotic 1 polypeptide. consists of at least 22 contiguous amino acids selected from the amino acid sequence shown in SEQ ID NO:2.

Yet another embodiment of the invention provides an hph1 fusion protein. The hph1 fusion protein comprises a first protein segment and a second protein segment fused together by means of a peptide bond. The first protein segment consists of at least 8 contiguous amino acids of a human polyhomeotic 1 protein.

Still another embodiment of the invention provides a preparation of antibodies which specifically bind to a human polyhomeotic 1 protein.

Even another embodiment of the invention provides an isolated and purified subgenomic polynucleotide. The isolated and purified subgenomic polynucleotide consists of at least 10 contiguous nucleotides selected from the nucleotide sequence shown in SEQ ID NO:1.

Yet another embodiment of the invention provides an expression construct for expressing all or a portion of a human polyhomeotic 1 protein. The expression construct comprises a promoter and a polynucleotide segment. The polynucleotide segment encodes at least 8 contiguous amino acids of a human polyhomeotic 1 protein. The polynucleotide segment is located downstream from the promoter. Transcription of the polynucleotide segment initiates at the promoter.

A further embodiment of the invention provides a homologously recombinant cell. The homologously recombinant cell is the result of introduction of a DNA construct, comprising a targeting sequence selected from the nucleotide sequence shown in SEQ ID NO:1, an exogenous regulatory sequence, an exogenous exon, and a splice donor site. A new transcription unit is formed by means of insertion of the DNA construct upstream to the coding sequence of an hph1 gene. The exogenous regulatory sequence directs transcription of the coding sequence of the hph1 gene in the recombinant cell. The new transcription unit can be used to turn the hph1 gene on or off as desired.

Still another embodiment of the invention provides a method of identifying a neoplastic tissue of a human. The method comprises comparing the expression of a polyhomeotic 1 gene in a first tissue of a human suspected of being neoplastic with the expression of a polyhomeotic 1 gene in a second tissue of the human which is normal. Overexpression of the human polyhomeotic 1 gene in the first tissue identifies the first tissue as being neoplastic.

Even another embodiment of the invention provides a method to aid in the diagnosis or prognosis of neoplasia in a human. The method comprises comparing a polyhomeotic 1 gene, mRNA, or protein in a first tissue of a human suspected of being neoplastic with a polyhomeotic 1 gene, mRNA, or protein in a second tissue of a human which is normal. A difference between the polyhomeotic 1 genes, mRNAs, or proteins in the first and second tissues indicates neoplasia in the first tissue.

Another embodiment of the invention provides a method to aid in detecting a genetic predisposition to neoplasia in a human. The method comprises comparing a polyhomeotic 1 gene, mRNA, or protein in the fetal tissue of a human with a wild-type human polyhomeotic 1 gene, mRNA, or protein. A difference between the polyhomeotic 1 gene, mRNA, or protein in the fetal tissue of the human and the wild-type human polyhomeotic 1 gene, mRNA, or protein indicates a genetic predisposition to neoplasia in the human.

Yet another embodiment of the invention provides method of identifying a human chromosome 12. The method comprises the steps of contacting a preparation of metaphase human chromosomes with a nucleotide probe comprising at least 12 contiguous nucleotides selected from the nucleotide sequence shown in SEQ ID NO:1 and detecting a region of a chromosome which specifically hybridizes to the nucleotide probe. A region of a chromosome which specifically hybridizes to the nucleotide probe is identified as a region of human chromosome 12.

A further embodiment of the invention provides a method of inducing a cell to de-differentiate. The method comprises the step of contacting a differentiated cell with a composition comprising all or a portion of a human polyhomeotic 1 gene or expression product. Said all or a portion of the human polyhomeotic 1 gene or expression product is capable of inducing de-differentiation of the cell.

The present invention thus provides the art with a novel human oncogene, called "polyhomeotic 1" (hph1). The hph1 gene and protein can be used, inter alia, as therapeutic and diagnostic tools for proliferative and developmental disorders and to identify a p13 region of a human chromosome 12.

DETAILED DESCRIPTION OF THE PREFERRED EMBODIMENTS

It is a discovery of the present invention that hph1 functions as an oncogene and thus is implicated in neoplastic disorders. The hph1 gene, protein, and mRNA can be used as a diagnostic tool for these disorders. Coding sequences of hph1 can also be used to identify human chromosome 12.

The coding region of the hph1 gene has the nucleotide sequence shown in SEQ ID NO:1. Other (degenerate) sequence encoding the same amino acid sequence and those nucleotide sequences which vary by up to 10% are included herein. Typically these can be confirmed by hybridization under stringent conditions. The hph1 gene maps to human chromosome 12p13, a region frequently amplified in association with the progression of glioma. While not wanting to be bound by any particular theory, it is believed that there are lethal alleles of hph1 which are involved in neoplasias, such as gliomas and glioblastomas.

Human polyhomeotic 1 protein has the amino acid sequence shown in SEQ ID NO:2. Any naturally occurring variants of this sequence that may occur in human tissues and which have oncogenic activity are within the scope of this invention. Thus, reference herein to either the nucleotide or amino acid sequence of hph1 includes reference to naturally occurring variants of these sequences. Nonnaturally occurring variants which differ by as much as four amino acids and retain biological function are also included here. Preferably the changes are conservative amino acid changes, i.e., changes of similarly charged or uncharged amino acids.

Figure 1:
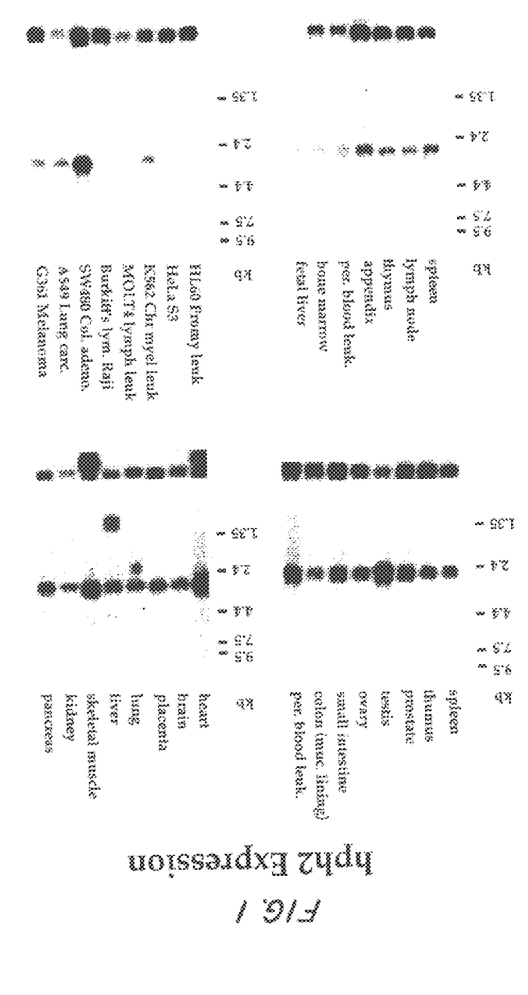
FIG. 1. Northern blots probed with an hph1 nucleotide probe. The figure depicts hph1 mRNA expression in human tissues and cancer cell lines.

Human polyhomeotic 1 mRNA comprises two major transcripts which measure 4.4 kb and 6.5 kb on Northern blots of human polyA+RNA probed with an hph1 nucleotide probe (FIG. 1). The 4.4 and 6.5 kb transcripts are expressed, inter alia, at highest levels in adult thymus and testis; at lower levels in the heart, prostate, ovary, small intestine, peripheral blood lymphocytes, skeletal muscle, and pancreas; and at very low levels in the lung, liver, and kidney. The 4.4 and 6.5 kb hph1 mRNA transcripts are also expressed in human cancer cell lines, such as SW480 (colon carcinoma), G361 (melanoma), and Burkitt's lymphoma Raji.

Human polyhomeotic 1 polypeptides comprise at least 22, 25, 30, or 35 contiguous amino acids of the amino acid sequence shown in SEQ ID NO:2. Both full-length hph1 protein and hph1 polypeptides are useful for generating antibodies against hph1 amino acid sequences. Human polyhomeotic 1 proteins and polypeptides can be isolated and purified from human cells such as thymus, testis, heart, prostate, ovary, small intestine, peripheral blood lymphocytes, skeletal muscle, pancreas, lung, liver, and kidney. Preferably, the protein or polypeptides are purified from thymus or testis.

Polyhomeotic 1 proteins or polypeptides can be purified by any method known in the art. These methods include, but are not limited to, size exclusion chromatography, ammonium sulfate fractionation, ion exchange chromatography, affinity chromatography, crystallization, electrofocusing, and preparative gel electrophoresis. The skilled artisan can readily select methods which will result in a preparation of hph1 protein or polypeptide which is substantially free from other proteins and from carbohydrates, lipids, or subcellular organelles. A preparation of isolated and purified hph1 protein is at least 80% pure; preferably, the preparations are 90%, 95%, or 99% pure. Purity of the preparations may be assessed by any means known in the art, such as SDS-polyacrylamide gel electrophoresis.

Polyhomeotic 1 proteins and polypeptides can be produced by recombinant DNA methods or by synthetic chemical methods. For production of recombinant hph1 proteins or polypeptides, hph1 coding sequences selected from the nucleotide sequence shown in SEQ ID NO:1 can be expressed in known prokaryotic or eukaryotic expression systems. Bacterial, yeast, insect, or mammalian expression systems can be used, as is known in the art. Synthetic chemical methods, such as solid phase peptide synthesis, can be used to synthesize hph1 protein or polypeptides.

Fusion proteins containing at least eight contiguous hph1 amino acids can also be constructed. Human polyhomeotic 1 fusion proteins are useful for generating antibodies against hph1 amino acid sequences and for use in various assay systems. For example, hph1 fusion proteins can be used to identify proteins which interact with hph1 protein and influence its function. Physical methods, such as protein affinity chromatography, or library-based assays for protein-protein interactions, such as the yeast two-hybrid or phage display systems, can be used for this purpose. Such methods are well known in the art, and can be used inter alia as drug screens.

An hph1 fusion protein comprises two protein segments fused together by means of a peptide bond. The first protein segment comprises at least 8, 10, 12, 15, or 20 contiguous amino acids of an hph1 protein. The amino acids can be selected from the amino acid sequence shown in SEQ ID NO:2 or from a naturally or nonnaturally occurring, biologically active variant of that sequence. The first protein segment can also be a full-length hph1 protein. The second protein segment can be a full-length protein or a protein fragment or polypeptide. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase or other enzymes which are known in the art.

Techniques for making fusion proteins, either recombinantly or by covalently linking two protein segments, are also well known. Recombinant DNA methods can be used to construct hph1 fusion proteins, for example, by making a DNA construct which comprises hph1 coding sequences selected from SEQ ID NO:1 in proper reading frame with nucleotides encoding the second protein segment and expressing the DNA construct in a host cell, as described below.

Isolated and purified hph1 proteins, polypeptides, or fusion proteins can be used as immunogens, to obtain a preparation of antibodies which specifically bind to an hph1 protein. The antibodies can be used to detect wild-type hph1 proteins in human tissue. The antibodies can also be used to detect the presence of mutations in the hph1 gene which results in overexpression of the hph1 protein or in hph1 proteins with altered size or electrophoretic mobilities.

Preparations of polyclonal and monoclonal hph1 antibodies can be made using standard methods known in the art. The antibodies specifically bind to epitopes present in hph1 proteins having the amino acid sequence shown in SEQ ID NO:2. Preferably, the hph1 epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids. Antibodies which specifically bind to hph1 proteins provide a detection signal at least 5-, 10-, or 20-fold higher than a detection signal provided with other proteins when used in Western blots or other immunochemical assays. Preferably, antibodies which specifically bind hph1 proteins do not detect other proteins in immunochemical assays and can immunoprecipitate hph1 proteins from solution.

Human polyhomeotic 1 antibodies can be purified by methods well known in the art. Preferably, the antibodies are affinity purified, by passing antiserum over a column to which an hph1 protein, polypeptide, or fusion protein is bound. The bound antibodies can then be eluted from the column, for example using a buffer with a high salt concentration.

Purified and isolated hph1 subgenomic polynucleotides can be used, inter alia, as primers to obtain additional copies of the polynucleotides, to express hph1 mRNA, protein, polypeptides, or fusion proteins, and as probes for identifying wild-type and mutant hph1 coding sequences. The probes can also be used to identify the short arm of a human chromosome 12, as described below.

Purified and isolated hph1 subgenomic polynucleotides of the invention comprise at least 10 contiguous nucleotides selected from SEQ ID NO:1. Subgenomic hph1 polynucleotides according to the invention contain less than a whole chromosome. Preferably, the polynucleotides are intron-free.

Subgenomic hph1 polynucleotides can be isolated and purified free from other nucleotide sequences using standard nucleic acid purification techniques. For example, restriction enzymes and probes can be used to isolate polynucleotide fragments which comprise the hph1 coding sequences. Isolated polynucleotides are in preparations which are free or at least 90% free of other molecules.

Complementary DNA encoding hph1 proteins can be made using reverse transcriptase, with hph1 mRNA as a template. The polymerase chain reaction (PCR) can be used to obtain the polynucleotides, using either human genomic DNA or cDNA as a template. Alternatively, synthetic chemistry techniques can be used to synthesize the polynucleotide molecules of the invention. The degeneracy of the genetic code allows alternate nucleotide sequences to be synthesized which will encode a polyhomeotic 1 protein having the amino acid sequence shown in SEQ ID NO:2. All such nucleotide sequences are within the scope of the present invention.

A number of terms used in the art of genetic engineering and protein chemistry are used herein with the following defined meanings.

Two nucleic acid fragments are "homologous" if they are capable of hybridizing to one another under hybridization conditions described in Maniatis et al., op. cit., pp. 320–323. However, by using the following wash conditions—2X SSC, 0.1% SDS, room temperature twice, 30 minutes each; then 2X SSC, 0.1% SDS, 50° C. once, 30 minutes; then 2X SSC, room temperature twice, 10 minutes each—homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

A DNA fragment is "derived from" an hph1-encoding DNA sequence if it has the same or substantially the same basepair sequence as a region of the coding sequence of the entire hph1 molecule. Preferably the DNA sequence has at least 95% or preferably 98% or 99% identity with hph1.

Substantially the same means, when referring to biological activities, that the activities are of the same type although they may differ in degree. When referring to amino acid sequences, substantially the same means that the molecules in question have similar biological properties and preferably have at least 85%, 90%, or 95% homology in amino acid sequences. More preferably, the amino acid sequences are at least 98% identical. In other uses, substantially the same has its ordinary English language meaning.

A protein is "derived from" an hph1 molecule if it has the same or substantially the same amino acid sequence as a region of the hph1 molecule.

Protein hph1 both glycosylated and unglycosylated, or polypeptide derivatives thereof, may be used for producing antibodies, either monoclonal or polyclonal, specific to hph1. By polypeptide derivatives is meant polypeptides differing in length from natural hph1 and containing five or more amino acids from hph1 in the same primary order as found in hph1 as obtained from a natural source. Polypeptide molecules having substantially the same amino acid sequence as Hph1 but possessing minor amino acid substitutions that do not substantially affect the ability of the Hph1 polypeptide derivatives to interact with Hph1-specific molecules, such as antibodies, are within the definition of Hph1. Derivatives include glycosylated forms, aggregative conjugates with other molecules and covalent conjugates with unrelated chemical moieties. Derivatives also include allelic variants, species variants, and muteins. Truncations or deletions of regions which do not affect biological function are also encompassed. Covalent derivatives are prepared by linkage of functionalities to groups which are found in the amino acid chain or at the N- or C-terminal residue by means known in the art.

Hph1-specific molecules include polypeptides such as antibodies that are specific for the Hph1 polypeptide containing the naturally occurring Hph1 amino acid sequence. By "specific binding polypeptide" is intended polypeptides that bind with Hph1 and its derivatives and which have a measurably higher binding affinity for the target polypeptide, i.e., Hph1 and polypeptide derivatives of Hph1, than for other polypeptides tested for binding. Higher affinity by a factor of 10 is preferred, more preferably a factor of 100. Binding affinity for antibodies refers to a single binding event (i.e., monovalent binding of an antibody molecule). Specific binding by antibodies also means that binding takes place at the normal binding site of the molecule's antibody (at the end of the arms in the variable region).

As discussed above, minor amino acid variations from the natural amino acid sequence of Hph1 are contemplated as being encompassed by the term Hph1; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysing, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid at a binding site involved in an interaction of Hph1. Whether an amino acid change results in a functional peptide can readily be determined by assaying the properties of the Hph1 polypeptide derivative.

An hph1 subgenomic polynucleotide of the present invention can be used in an expression construct, to express all or a portion of an hph1 protein in a host cell. The host cell comprising the expression construct can be prokaryotic or eukaryotic. A variety of host cells for use in bacterial, yeast, insect, and human expression systems are available and can be used to express the expression construct. The expression constructs can be introduced into the host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

The expression construct comprises a promoter which is functional in the particular host cell selected. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of an hph1 protein. The polynucleotide segment is located downstream from the promoter. Transcription of the polynucleotide segment initiates at the promoter. The expression construct can be linear or circular and can contain sequences, if desired, for autonomous replication.

The hph1 gene maps to human chromosome region 12p13. Thus, the subgenomic polynucleotides of the invention can be used to identify this chromosome region in metaphase spreads of human chromosomes. Preparations of human metaphase chromosomes can be prepared using standard cytogenetic techniques from human primary tissues or cell lines. Nucleotide probes comprising at least 12 contiguous nucleotides selected from the nucleotide sequence shown in SEQ ID NO:1 are used to identify the human chromosome. The nucleotide probes can be labeled, for example, with a radioactive, fluorescent, biotinylated, or chemiluminescent label, and detected by well known methods appropriate for the particular label selected. Protocols for hybridizing nucleotide probes to preparations of metaphase chromosomes are well known in the art. A nucleotide probe will hybridize specifically to nucleotide sequences in the chromosome preparations which are complementary to the nucleotide sequence of the probe. A probe which hybridizes specifically to human chromosome region 12p13 hybridizes to nucleotide sequences present in the hph1 gene and not to nucleotide sequences present in other human genes. A probe which hybridizes specifically to an hph1 gene provides a detection signal at least 5-, 10- or 20-fold higher than the background hybridization provided with non-hph1 coding sequences.

A human chromosome which specifically hybridizes to an hph1 nucleotide probe is identified as a human chromosome 12. Preferably, the nucleotide probe identifies the short arm of human chromosome 12. More preferably, the nucleotide probe identifies a p13 region of human chromosome 12. The present invention also provides a method to identify neoplastic tissue in a human. The expression of an hph1 gene can be compared between a first tissue which is suspected of being neoplastic and a second tissue of the human which is normal. The normal tissue can be any tissue of the human, especially those which express the hph1 gene including, but not limited to, thymus, testis, heart, prostate, ovary, small intestine, peripheral blood lymphocytes, skeletal muscle, pancreas, lung, liver, and kidney. The tissue suspected of being neoplastic can be derived from a different tissue type of the human, but preferably it is derived from the same tissue type, for example an intestinal polyp or other abnormal growth. A difference between the hph1 gene, mRNA, or protein in the two tissues which are compared, for example in molecular weight, amino acid or nucleotide sequence, or relative abundance, indicates a somatic mutation in the hph1 gene (or a gene which regulates it) in the tissue of the human which was suspected of being neoplastic.

The hph1 genes in the two tissues can be compared by any means known in the art. For example, the two genes can be sequenced, and the sequence of the hph1 gene in the tissue suspected of being neoplastic can be compared with the wild-type sequence in the normal tissue. The hph1 genes or portions of the hph1 genes in the two tissues can be amplified, for example using nucleotide primers selected from the nucleotide sequence shown in SEQ ID NO:1 in the polymerase chain reaction (PCR). The amplified genes or portions of genes can be hybridized to nucleotide probes selected from the nucleotide sequence shown in SEQ ID NO:1. The nucleotide probes can be labeled by a variety of methods, such as radiolabeling, biotinylation, or labeling with fluorescent or chemiluminescent tags, and detected by standard methods known in the art.

Alternatively, hph1 mRNA in the two tissues can be compared. PolyA+RNA can be isolated from the two tissues as is known in the art. For example, one of skill in the art can readily determine differences in the size or amount of hph1 mRNA transcripts between the two tissues that are compared, using Northern blots and nucleotide probes selected from the nucleotide sequence shown in SEQ ID NO:1. Overexpression of hph1 mRNA in a tissue sample suspected of being neoplastic compared with the expression of hph1 mRNA in a normal tissue is indicative of neoplasia.

Any method for analyzing proteins can be used to compare two hph1 proteins from matched samples. The sizes of the hph1 proteins in the two tissues can be compared, for example, using the antibodies of the present invention to detect hph1 proteins in Western blots of protein extracts from the two tissues. Other changes, such as expression levels and subcellular localization, can also be detected immunologically. A higher hph1 protein expression level in a tissue suspected of being neoplastic compared with the hph1 protein expression level in a normal tissue is indicative of neoplasia.

Similarly, comparison of hph1 gene sequences or of hph1 gene expression products, e.g., mRNA and protein, between a tissue of a human which is suspected of being neoplastic and a normal tissue of a human can be used to diagnose or prognose neoplasia in the human. Such comparisons of hph1 genes, mRNA, or protein can be made as described above. Overexpression of the hph1 gene in the tissue suspected of being neoplastic indicates neoplasia in the tissue. The degree of overexpression of the hph1 gene in the neoplastic tissue relative to wild-type expression of the gene in normal tissue, or differences in the amount of overexpression of the hph1 gene in the neoplastic tissue over time, can be used to prognose the progression of the neoplasia in that tissue or to monitor the response of the neoplastic tissue to various therapeutic regimens over time.

In addition, a genetic predisposition to neoplasia in a human can be detected by comparing a wild-type hph1 gene, mRNA, or protein with an hph1 gene, mRNA, or protein in a fetal tissue. Fetal tissues which can be used for this purpose include, but are not limited to, amniotic fluid, chorionic villi, blood, and the blastomere of an in vitro-fertilized embryo. The wild-type hph1 gene can be obtained from any tissue. The mRNA or protein can be obtained from a normal tissue of a human in which the hph1 gene is expressed. Such tissues are disclosed above. Differences such as alterations in the nucleotide sequence or size of the fetal hph1 gene or mRNA, or alterations in the molecular weight, amino acid sequence, or relative abundance of fetal hph1 protein indicate a germline mutation in the hph1 gene of the fetus which indicates a genetic predisposition to neoplasia.

The hph1 polynucleotide and amino acid sequences of the invention can also be used to induce de-differentiation of a differentiated cell, in order to study the process of oncogenesis and test compounds which affect this process. Differentiated cells which can be induced to de-differentiate using hph1 subgenomic polynucleotides, proteins, polypeptides, or fusion proteins include all differentiated human cells which express the hph1 gene, including thymus, testis, heart, prostate, ovary, small intestine, peripheral blood lymphocytes, skeletal muscle, pancreas, lung, liver, and kidney.

Expression of an endogenous hph1 gene in a cell can be altered by introducing in frame with the endogenous hph1 gene a DNA construct comprising a targeting sequence, a regulatory sequence, an exon, and an unpaired splice donor site by homologous recombination, such that a homologously recombinant cell comprising the DNA construct is formed. This method of affecting endogenous gene expression is taught in U.S. Pat. No. 5,641,670, which is incorporated herein in its entirety by reference. The targeting sequence is a segment of at least 10, 12, 15, 20, or 50 contiguous nucleotides selected from the nucleotide sequence shown in SEQ ID NO:1. The transcription unit is located upstream to a coding sequence of the endogenous hph1 gene. The exogenous regulatory sequence directs transcription of the coding sequence of the hph1 gene. Preferably, the homologously recombinant cell is a differentiated cell. In addition, it is preferred that the exogenous regulatory sequence directs decreased transcription of the coding sequence of the hph1 gene.

Cells transformed with wild-type hph1 subgenomic polynucleotides can be used as model systems to study oncogenesis and drug treatments which are effective in preventing transformation to an oncogenic phenotype. Oncogenesis is a process which involves alterations in gene expression in the transformed cells. These alterations in gene expression will be reflected in morphological and biochemical changes in the transformed cells. Morphological changes can be studied, for example, by observing the transformed cells microscopically and comparing the appearance of the transformed cells with cells which have not received a wild-type hph1 gene. Biochemical alterations can be studied, inter alia, by comparing the proteins which are expressed by the cells before and at various times after transformation with the wild-type hph1 gene. Methods of comparing proteins between two cells, such as using SDS polyacrylamide electrophoresis, are well known in the art. Cells transformed with a wild-type hph1 gene and in the process of becoming neoplastic can also be exposed to various drug treatments to determine which treatments promote the morphological or biochemical changes which accompany acquisition of the neoplastic phenotype.

Antisense polynucleotides of the hph1 gene can also be used to interfere with expression of the gene. The invention provides a therapeutic composition for inhibiting an hph1 oncogene function in a cell. Inhibition of hph1 expression suppresses neoplasia, dysplasia, or hyperplastic cell growth. The cell to be treated can be any cell of a human which expresses the hph1 oncogene, such as thymus, testis, heart, prostate, ovary, small intestine, peripheral blood lymphocytes, skeletal muscle, pancreas, lung, liver, and kidney. Such cells include neoplasias of the tissues mentioned above as well as any other neoplastic cells which have express polyhomeotic 1 oncogene function. The therapeutic composition comprises the antisense strand of all or a portion of human hph1 gene in a pharmaceutically acceptable carrier. The hph1 antisense product can be, e.g., mRNA or DNA.

Pharmaceutically acceptable carriers are well known to those in the art. Such carriers include, but are not limited to, large, slowly metabolized macromolecules such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat No. 5,422,120, WO 95/13796, WO 91/14445, or EP 524,968 B1, can also be used as a carrier for the therapeutic polyhomeotic 1 composition.

Typically, the antisense hph1 composition is prepared as an injectable, either as a liquid solution or suspension, however solid forms suitable for solution in, or suspension in, liquid vehicles prior to injection can also be prepared. The composition can also be formulated into an enteric coated tablet or gel capsule according to known methods in the art, such as those described in U.S. Pat No. 4,853,230, EP 225,189, AU 9,224,296, and AU 9,230,801.

Proliferative disorders, such as neoplasias, dysplasias, and hyperplasias, can be treated by administration of the antisense hph1 composition. Neoplasias which can be treated with the antisense composition include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, and metastatic tumors. Proliferative disorders which can be treated with the therapeutic composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias or pseudoepitheliomatous hyperplasia of the skin can be treated with antisense hph1 therapeutic compositions. Even in disorders in which hph1 mutations are not implicated, downregulation or inhibition of hph1 expression can have therapeutic application. In these disorders, decreasing hph1 expression can help to suppress tumors. Similarly, in tumors where hph1 expression is not aberrant, effecting hph1 downregulation can suppress metastases.

Both the dose of the antisense hph1 composition and the means of administration can be determined based on the specific qualities of the therapeutic composition, the condition, age, and weight of the patient, the progression of the disease, and other relevant factors. Administration of the therapeutic antisense agents of the invention can include local or systemic administration, including injection, oral administration, particle gun or catheterized administration, and topical administration. Preferably, the therapeutic antisense composition contains an expression construct comprising a promoter and a polynucleotide segment of at least 12, 22, 25, 30, or 35 contiguous nucleotides of the antisense strand of hph1. Within the expression construct, the polynucleotide segment is located downstream from the promoter, and transcription of the polynucleotide segment initiates at the promoter. Various methods can be used to administer the therapeutic composition directly to a specific site in the body. For example, a small metastatic lesion can be located and the therapeutic composition injected several times in several different locations within the body of tumor. Alternatively, arteries which serve a tumor can be identified, and the therapeutic composition injected into such an artery, in order to deliver the composition directly into the tumor. A tumor which has a necrotic center an be aspirated and the composition injected directly into the now empty center of the tumor. The antisense hph1 composition can be directly administered to the surface of the tumor, for example, by topical application of the composition. X-ray imaging can be used to assist in certain of the above delivery methods.

Receptor-mediated targeted delivery of therapeutic compositions containing hph1 subgenomic antisense polynucleotides to specific tissues can also be used. Receptor-mediated DNA delivery techniques are described in, for example, Findeis et al. (1993), *Trends in Biotechnol.* 11, 202–05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Alternatively, the composition containing subgenomic antisense hph1 polynucleotides can be introduced into human cells ex vivo and then replaced into the human. Cells can be removed from a variety of locations including, for example, from a selected tumor or from an affected organ. In addition, the therapeutic antisense composition can be inserted into non-tumorigenic cells, for example, dermal fibroblasts or peripheral blood leukocytes. If desired, particular fractions of cells such as a T cell subset or stem cells can also be specifically removed from the blood (see, for example, PCT WO 91/16116). The hph1 antisense-containing therapeutic composition can then be contacted with the removed cells utilizing any of the above-described techniques, followed by the return of the cells to the human, preferably to or within the vicinity of a tumor. The above-described methods can additionally comprise the steps of depleting fibroblasts or other non-contaminating tumor cells subsequent to removing tumor cells from a human, and/or the step of inactivating the cells, for example, by irradiation.

Therapeutic compositions containing hph1 subgenomic antisense polynucleotides can be administered in a range of about 100 ng to about 200 mg of DNA for local administration in a gene therapy protocol. Concentration ranges of about 500 ng to about 50 mg, about 1 $\mu$g to about 2 mg, about 5 $\mu$g to about 500 $\mu$g, and about 20 $\mu$g to about 100 $\mu$g of DNA can also be used during a gene therapy protocol. Factors such as method of action and efficacy of transformation and expression are considerations that will effect the dosage required for ultimate efficacy of the hph1 subgenomic antisense polynucleotides. Where greater expression is desired over a larger area of tissue, larger amounts of hph1 subgenomic antisense polynucleotides or the same amounts readministered in a successive protocol of administrations, or several administrations to different adjacent or close tissue portions of for example, a tumor site, may be required to effect a positive therapeutic outcome. In all cases, routine experimentation in clinical trials will determine specific ranges for optimal therapeutic effect.

The hph1 therapeutic antisense composition can also be used to induce differentiation of a progenitor cell, e.g. in order to study the process of differentiation and test compounds which affect this process. Induction of differentiation is also desirable, for example, in the treatment of anaplastic tumors, which are composed of cells which have lost some of their differentiated characteristics. Progenitor cells which can be induced to differentiate using an hph1 therapeutic antisense composition comprising hph1 subgenomic antisense polynucleotides include, but are not limited to, erythropoietic stem cells, neuroblasts, chrondroblasts, melanoblasts, myoblasts, and neural crest cells. Antisense polynucleotides are typically generated within the cell by expression from antisense constructs which contain the antisense strand as the transcribed strand from a promoter. Thus antisense polynucleotides are transcribed within the cell which will bind and/or interfere with the translation of hph1 mRNA.

A more complete description of gene therapy vectors, especially retroviral vectors is contained in U.S. Ser. No. 08/869,309, which is expressly incorporated herein.

What is claimed is:

1. An isolated and purified subgenomic polynucleotide comprising the nucleotide sequence shown in SEQ ID NO:1.

2. An expression construct for expressing a human polyhomeotic 1 protein, comprising:
   a promoter; and
   a polynucleotide segment encoding a human polyhomeotic 1 protein as shown in SEQ ID NO:2, wherein the polynucleotide segment is located downstream from the promoter, wherein transcription of the polynucleotide segment initiates at the promoter.

3. A homologously recombinant cell having incorporated therein a new transcription initiation unit, wherein the new transcription initiation unit comprises:
   (a) an exogenous regulatory sequence,
   (b) an exogenous exon; and
   (c) a splice donor site, wherein the transcription initiation unit is located upstream of a coding sequence of an hph1 gene as shown in SEQ ID NO:1, wherein the exogenous regulatory sequence directs transcription of the coding sequence of the hph1 gene.

4. An isolated and purified subgenomic polynucleotide, comprising a polynucleotide segment encoding a human polyhomeotic 1 protein as shown in SEQ ID NO:2, wherein a single strand of the subgenomic polynucleotide hybridizes to the nucleotide sequence shown in SEQ ID NO:1 with no more than 25–30% basepair mismatches.

5. The isolated and purified subgenomic polynucleotide of claim 4 wherein a single strand of the subgenomic polynucleotide hybridizes to the nucleotide sequence shown in SEQ ID NO:1 with no more than 15–25% basepair mismatches.

6. The isolated and purified subgenomic polynucleotide of claim 4 wherein a single strand of the subgenomic polynucleotide hybridizes to the nucleotide sequence shown in SEQ ID NO:1 with no more than 5–15% basepair mismatches.

7. The isolated and purified subgenomic polynucleotide of claim 1 wherein the nucleotide sequence is the nucleotide sequence shown in SEQ ID NO:1.

8. An expression construct for expressing a human polyhomeotic 1 protein, comprising:
   a promoter; and
   a polynucleotide segment encoding a human polyhomeotic 1 protein as shown in SEQ ID NO:2, wherein a single strand of the polynucleotide segment hybridizes to the nucleotide sequence shown in SEQ ID NO:1 with no more than 25–30% basepair mismatches.

9. The expression construct of claim 8 wherein a single strand of the polynucleotide segment hybridizes to the nucleotide sequence shown in SEQ ID NO:1 with no more than 15–25% basepair mismatches.

10. The expression construct of claim 8 wherein a single strand of the polynucleotide segment hybridizes to the nucleotide sequence shown in SEQ ID NO:1 with no more than 5–15% basepair mismatches.

11. An isolated and purified subgenomic polynucleotide, comprising a polynucleotide segment encoding a human polyhomeotic 1 protein as shown in SEQ ID NO:2, wherein a single strand of the subgenomic polynucleotide hybridizes to the nucleotide sequence shown in SEQ ID NO:1 after washing in 2X SSC, 0.1% SDS at room temperature twice for thirty minutes, 2X SSC, 0.1% SDS at 50° C. for thirty minutes, and 2X SSC at room temperature twice for ten minutes.

12. An expression construct for expressing a human polyhomeotic 1 protein, comprising:
   a promoter; and a polynucleotide segment encoding a human polyhomeotic 1 protein as shown in SEQ ID NO:2, wherein a single strand of the polynucleotide segment hybridizes to the nucleotide sequence in SEQ ID NO:1 after washing in 2X SSC, 0.1% SDS at room temperature twice for thirty minutes, 2X SSC, 0.1% SDS at 50° C. for thirty minutes, and 2X SSC at room temperature twice for ten minutes.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 3879 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
ATGGAGACTG AGAGCGAGCA GAACTCCAAT TCCACCAATG GGAGTTCTAG CTCAGGGGGC      60
AGCTCTCGGC CCCAGATAGC TCAAATGTCA CTATATGAAC GACAAGCAGT GCAGGCTCTG     120
CAAGCACTGC AGCGGCAGCC CAATGCAGCT CAGTATTTCC ACCAGTTCAT GCTCCAGCAG     180
CAGCTCAGTA ATGCCCAGCT GCATAGCCTG GCTGCCGTCC AGCAGGCCAC AATTGCTGCC     240
AGTCGGCAGG CCAGCTCCCC AAACACCAGC ACTACACAGC AGCAGACTAC CACCACCCAG     300
GCCTCGATCA ATCTGGCCAC CACATCGGCC GCCCAGCTCA TCAGCCGATC CCAGAGTGTG     360
AGCTCTCCTA GTGCTACCAC CTTGACCCAA TCTGTGCTAC TGGGGAACAC CACCTCCCCA     420
CCCCTCAACC AGTCTCAGGC CCAGATGTAT CTACGGCCAC AGCTGGGAAA CCTATTGCAG     480
GTAAACCGAA CCCTGGGTCG GAATGTGCCT CTAGCCTCCC AACTCATCCT GATGCCTAAT     540
GGGGCGGTGG CTGCAGTCCA GCAGGAGGTG CCATCTGCTC AGTCTCCTGG AGTTCATGCA     600
GATGCAGATC AGGTTCAGAA CTTGGCAGTA AGGAATCAAC AGGCCTCAGC TCAAGGACCT     660
CAGATGCAAG GCTCCACTCA GAAGGCCATT CCTCCAGGAG CCTCCCCTGT CTCTAGCCTC     720
TCCCAGGCCT CTAGCCAGGC CCTAGCGGTG GCACAGGCTT CCTCTGGGGC CACAAACCAG     780
TCCCTCAACC TTAGTCAAGC TGGTGGAGGC AGTGGGAATA GCATCCCAGG GTCCATGGGT     840
CCAGGTGGAG GTGGGCAGGC ACATGGTGGT TTGGGTCAGT TGCCTTCCTC AGGAATGGGT     900
GGTGGGAGCT GTCCCAGGAA GGGTACAGGA GTGGTGCAGC CCTTGCCTGC AGCCCAAACA     960
GTGACTGTGA GCCAGGGCAG CCAGACAGAG GCAGAAAGTG CAGCAGCCAA GAAGGCAGAA    1020
GCAGATGGGA GTGGCCAGCA GAATGTGGGC ATGAACCTGA CACGGACAGC CACACCTGCG    1080
CCCAGCCAGA CACTTATTAG CTCAGCCACC TACACACAGA TCCAGCCCCA TTCACTGATT    1140
CAGCAACAGC AACAGATCCA CCTCCAGCAG AAACAGGTGG TGATCCAGCA GCAGATTGCC    1200
ATCCACCACC AGCAGCAGTT CCAGCACCGG CAGTCCCAGC TCCTTCACAC AGCTACACAC    1260
CTCCAGTTGG CGCAGCAGCA GCAGCAGCAA CAACAGCAAC AGCAGCAACA GCAGCAGCCG    1320
CAAGCCACCA CCCTCACTGC CCCTCAGCCA CCACAGGTCC CACCTACTCA GCAGGTCCCA    1380
CCTTCCCAGT CCCAGCAGCA AGCCCAAACC CTGGTCGTTC AGCCCATGCT TCAGTCTTCA    1440
CCCTTGTCTC TTCCACCTGA TGCAGCCCCT AAGCCACCAA TTCCCATCCA ATCCAAACCA    1500
CCTGTAGCAC CTATCAAGCC GCCTCAGTTA GGGGCCGCTA AGATGTCAGC TGCCCAGCAA    1560
CCACCACCCC ATATCCCTGT GCAAGTTGTA GGCACTGAC AGCCAGGTAC AGCCCAGGCA     1620
CAGGCTTTGG GGTTGGCACA GCTGGCAGCT GCTGTACCTA CTTCCCGGGG GATGCCAGGT    1680
ACAGTGCAGT CTGGTCAGGC CCATTTGGCC TCCTCGCCAC CTTCATCCCA GGCTCCTGGT    1740
GCACTGCAGG AGTGCCCTCC CACATTGGCC CCTGGGATGA CCCTTGCTCC TGTGCAGGGG    1800
```

```
ACAGCACATG TGGTAAAGGG TGGGGCTACC ACCTCCTCAC CTGTTGTAGC CCAGGTCCCT      1860

GCTGCCTTCT ATATGCAGTC TGTGCACTTG CCGGGTAAAC CCCAGACATT GGCTGTCAAA      1920

CGCAAGGCTG ACTCTGAGGA GGAGAGAGAT GATGTCTCCA CATTGGGTTC AATGCTTCCT      1980

GCCAAAGCAT CTCCAGTAGC AGAAAGCCCA AAAGTCATGG ACGAGAAGAG CAGTCTTGGA      2040

GAAAAAGCTG AATCAGTGGC TAATGTGAAT GCTAATACTC CAAGCAGTGA ACTAGTAGCC      2100

TTGACCCCCG CCCCTTCAGT ACCGCCTCCT ACACTAGCCA TGGTGTCTAG ACAAATGGGT      2160

GACTCAAAAC CCCCACAGGC CATCGTGAAG CCCCAGATTC TCACCCACAT CATTGAAGGC      2220

TTTGTTATCC AGGAAGGAGC AGAACCTTTC CCGGTGGGTT GTTCTCAGTT ACTGAAGGAG      2280

TCTGAGAAGC CACTACAGAC TGGCCTTCCG ACAGGGCTGA CTGAGAATCA GTCAGGTGGC      2340

CCTTTGGGAG TGGACAGCCC ATCTGCTGAG TTAGATAAGA AGGCGAATCT CCTGAAGTGC      2400

GAGTACTGTG GAAGTACGC CCCCGCAGAG CAGTTTCGTG GCTCTAAGAG GTTCTGCTCC      2460

ATGACTTGCG CTAAGAGGTA CAATGTGAGC TGTAGCCATC AGTTCCGGCT GAAGAGGAAA      2520

AAAATGAAAG AGTTTCAAGA AGCCAACTAT GCTCGCGTTC GCAGGCGTGG ACCCCGCCGC      2580

AGCTCCTCTG ACATTGCCCG TGCCAAGATT CAGGGCAAGT GCCACCGGGG TCAAGAAGAC      2640

TCTAGCCGGG GTTCAGATAA TTCCAGTTAT GATGAAGCAC TCTCTCCAAC ATCTCCTGGG      2700

CCTTTATCAG TAAGAGCTGG GCATGGAGAA CGTGACCTGG GGAATCCCAA TACAGCTCCA      2760

CCTACACCGG AATTACATGG CATCAACCCT GTGTTCCTGT CCAGTAATCC CAGCCGTTGG      2820

AGTGTAGAGG AGGTGTACGA GTTTATTGCT TCTCTCCAAG GCTGCCAAGA GATTGCAGAG      2880

GAATTTCGCT CACAGGAGAT TGATGGACAG GCCCTTTTAT TACTTAAAGA AGAACATCTT      2940

ATGAGTGCCA TGAACATCAA GCTGGGCCCT GCCCTCAAGA TCTGCGCCAA GATAAATGTC      3000

CTCAAGGAGA CCTAAGGTGG CCCTCTTGCA CAAACCAGCC TAAGGCAGAC ACTCTCCACT      3060

GTCCAGGTTA TAACCTGGTA CCAGCAGACT TTGCAGGGAA GAAAGAGTTG TTCCAATCAT      3120

GTAACCTTCT GTAGGGGATT ACTGAGACAG GGAAGAGAAG TGCAAGAATT GGTTGCTGGT      3180

GCTACATGGC GGCAGCTTTG ACATTTTCTC TGGGTTCTAC TTTATTTTTT AAAATCTTTA      3240

CAGTTCTCAC CATTTCACGT ACCTTAATCC AATCTTTATA AAAGAGGCAG TCTAGAGAAC      3300

TAGGACTGCT CAGCCTTATC CTGGAGTGGA GCATTTAGCC CAGGTCTTAA TTCTCCAAGA      3360

GGAGGAATAC ATAGTATGGT AAGGCAAGGA ACTGGGTGGA ATGTCAGGTT GCCTGCCCAA      3420

TGGGAGAGGT AGGGTTTTTC TAGCTTGTGT GACAGAAGTA GCAAAATCTG GTCCTCCCCC      3480

CTCCCAGTGT AGCTGTGGCT CAGAGTTTTT TCTTTTTGTT GTCACTTACT CCCTTGTGAT      3540

TGAATTTTTT CTCCTGCATC CATGGCAGGA TCCCCAGCCA GTATAGAGAC TTGGTTGGCA      3600

TCTTCTGCTG CAGGGACTAA AAGTATTTGA CTGGGGCACA TGTGGCTGTT GTCATTCTTT      3660

CTGCATCCCA CTGTTCCCCT CCAATTTATG TTATTTTCTA CCCTGTTTTT CAGTTCCATC      3720

TCTGCTCTGT CCTATAGCTT TATAAAACCA GAGTGTGTGG GGCTGAGGTC AGGAGTATAA      3780

GTACCTGCCT TAGGCACTAT TCCTTATATA ACAAAAATAT TAAATATTTT TTTCCTCAGT      3840

AAAAGGATGA AAATTGGTAA AAAAAAAAAA AAAAAAAGG                             3879
```

(2) INFORMATION FOR SEQ ID NO:2:

(i) SEQUENCE CHARACTERISTICS:
        (A) LENGTH: 1004 amino acids
        (B) TYPE: amino acid
        (C) STRANDEDNESS: single
        (D) TOPOLOGY: linear -continued (ii) MOLECULE TYPE: protein (xi) SEQUENCE DESCRIPTION: SEQ ID NO:2:

```
Met Glu Thr Glu Ser Glu Gln Asn Ser Asn Ser Thr Asn Gly Ser Ser
 1               5                  10                  15

Ser Ser Gly Gly Ser Ser Arg Pro Gln Ile Ala Gln Met Ser Leu Tyr
            20                  25                  30

Glu Arg Gln Ala Val Gln Ala Leu Gln Ala Leu Gln Arg Gln Pro Asn
        35                  40                  45

Ala Ala Gln Tyr Phe His Gln Phe Met Leu Gln Gln Leu Ser Asn
    50                  55                  60

Ala Gln Leu His Ser Leu Ala Ala Val Gln Gln Ala Thr Ile Ala Ala
65                  70                  75                  80

Ser Arg Gln Ala Ser Ser Pro Asn Thr Ser Thr Gln Gln Thr
            85                  90                  95

Thr Thr Thr Gln Ala Ser Ile Asn Leu Ala Thr Thr Ser Ala Ala Gln
            100                 105                 110

Leu Ile Ser Arg Ser Gln Ser Val Ser Ser Pro Ser Ala Thr Thr Leu
            115                 120                 125

Thr Gln Ser Val Leu Leu Gly Asn Thr Thr Ser Pro Pro Leu Asn Gln
            130                 135                 140

Ser Gln Ala Gln Met Tyr Leu Arg Pro Gln Leu Gly Asn Leu Leu Gln
145                 150                 155                 160

Val Asn Arg Thr Leu Gly Arg Asn Val Pro Leu Ala Ser Gln Leu Ile
                165                 170                 175

Leu Met Pro Asn Gly Ala Val Ala Ala Val Gln Gln Glu Val Pro Ser
            180                 185                 190

Ala Gln Ser Pro Gly Val His Ala Asp Ala Asp Gln Val Gln Asn Leu
            195                 200                 205

Ala Val Arg Asn Gln Gln Ala Ser Ala Gln Gly Pro Gln Met Gln Gly
            210                 215                 220

Ser Thr Gln Lys Ala Ile Pro Pro Gly Ala Pro Val Ser Ser Leu
225                 230                 235                 240

Ser Gln Ala Ser Ser Gln Ala Leu Ala Val Ala Gln Ala Ser Ser Gly
            245                 250                 255

Ala Thr Asn Gln Ser Leu Asn Leu Ser Gln Ala Gly Gly Ser Gly
            260                 265                 270

Asn Ser Ile Pro Gly Ser Met Gly Pro Gly Gly Gly Gln Ala His
            275                 280                 285

Gly Gly Leu Gly Gln Leu Pro Ser Ser Gly Met Gly Gly Gly Ser Cys
            290                 295                 300

Pro Arg Lys Gly Thr Gly Val Val Gln Pro Leu Pro Ala Ala Gln Thr
305                 310                 315                 320

Val Thr Val Ser Gln Gly Ser Gln Thr Glu Ala Glu Ser Ala Ala Ala
            325                 330                 335

Lys Lys Ala Glu Ala Asp Gly Ser Gly Gln Gln Asn Val Gly Met Asn
            340                 345                 350

Leu Thr Arg Thr Ala Thr Pro Ala Pro Ser Gln Thr Leu Ile Ser Ser
            355                 360                 365

Ala Thr Tyr Thr Gln Ile Gln Pro His Ser Leu Ile Gln Gln Gln Gln
            370                 375                 380

Gln Ile His Leu Gln Gln Lys Gln Val Val Ile Gln Gln Gln Ile Ala
385                 390                 395                 400
```

-continued

```
Ile His His Gln Gln Gln Phe Gln His Arg Gln Ser Gln Leu Leu His
                405                 410                 415
Thr Ala Thr His Leu Gln Leu Ala Gln Gln Gln Gln Gln Gln Gln Gln
            420                 425                 430
Gln Gln Gln Gln Gln Gln Gln Pro Gln Ala Thr Thr Leu Thr Ala Pro
        435                 440                 445
Gln Pro Pro Gln Val Pro Pro Thr Gln Gln Val Pro Pro Ser Gln Ser
    450                 455                 460
Gln Gln Gln Ala Gln Thr Leu Val Val Gln Pro Met Leu Gln Ser Ser
465                 470                 475                 480
Pro Leu Ser Leu Pro Pro Asp Ala Ala Pro Lys Pro Pro Ile Pro Ile
                485                 490                 495
Gln Ser Lys Pro Pro Val Ala Pro Ile Lys Pro Pro Gln Leu Gly Ala
            500                 505                 510
Ala Lys Met Ser Ala Ala Gln Pro Pro His Ile Pro Val Gln
        515                 520                 525
Val Val Gly Thr Arg Gln Pro Gly Thr Ala Gln Ala Gln Ala Leu Gly
    530                 535                 540
Leu Ala Gln Leu Ala Ala Ala Val Pro Thr Ser Arg Gly Met Pro Gly
545                 550                 555                 560
Thr Val Gln Ser Gly Gln Ala His Leu Ala Ser Ser Pro Pro Ser Ser
                565                 570                 575
Gln Ala Pro Gly Ala Leu Gln Glu Cys Pro Pro Thr Leu Ala Pro Gly
            580                 585                 590
Met Thr Leu Ala Pro Val Gln Gly Thr Ala His Val Val Lys Gly Gly
        595                 600                 605
Ala Thr Thr Ser Ser Pro Val Val Ala Gln Val Pro Ala Ala Phe Tyr
    610                 615                 620
Met Gln Ser Val His Leu Pro Gly Lys Pro Gln Thr Leu Ala Val Lys
625                 630                 635                 640
Arg Lys Ala Asp Ser Glu Glu Arg Asp Asp Val Ser Thr Leu Gly
                645                 650                 655
Ser Met Leu Pro Ala Lys Ala Ser Pro Val Ala Glu Ser Pro Lys Val
            660                 665                 670
Met Asp Glu Lys Ser Ser Leu Gly Glu Lys Ala Glu Ser Val Ala Asn
        675                 680                 685
Val Asn Ala Asn Thr Pro Ser Ser Glu Leu Val Ala Leu Thr Pro Ala
    690                 695                 700
Pro Ser Val Pro Pro Pro Thr Leu Ala Met Val Ser Arg Gln Met Gly
705                 710                 715                 720
Asp Ser Lys Pro Pro Gln Ala Ile Val Lys Pro Gln Ile Leu Thr His
                725                 730                 735
Ile Ile Glu Gly Phe Val Ile Gln Glu Gly Ala Glu Pro Phe Pro Val
            740                 745                 750
Gly Cys Ser Gln Leu Leu Lys Ser Glu Lys Pro Leu Gln Thr Gly
        755                 760                 765
Leu Pro Thr Gly Leu Thr Glu Asn Gln Ser Gly Gly Pro Leu Gly Val
    770                 775                 780
Asp Ser Pro Ser Ala Glu Leu Asp Lys Lys Ala Asn Leu Leu Lys Cys
785                 790                 795                 800
Glu Tyr Cys Gly Lys Tyr Ala Pro Ala Glu Gln Phe Arg Gly Ser Lys
                805                 810                 815
```

```
Arg Phe Cys Ser Met Thr Cys Ala Lys Arg Tyr Asn Val Ser Cys Ser
            820                 825                 830

His Gln Phe Arg Leu Lys Arg Lys Lys Met Lys Glu Phe Gln Glu Ala
            835                 840                 845

Asn Tyr Ala Arg Val Arg Arg Arg Gly Pro Arg Arg Ser Ser Ser Asp
    850                 855                 860

Ile Ala Arg Ala Lys Ile Gln Gly Lys Cys His Arg Gly Gln Glu Asp
865                 870                 875                 880

Ser Ser Arg Gly Ser Asp Asn Ser Ser Tyr Asp Glu Ala Leu Ser Pro
                885                 890                 895

Thr Ser Pro Gly Pro Leu Ser Val Arg Ala Gly His Gly Glu Arg Asp
            900                 905                 910

Leu Gly Asn Pro Asn Thr Ala Pro Pro Thr Pro Glu Leu His Gly Ile
            915                 920                 925

Asn Pro Val Phe Leu Ser Ser Asn Pro Ser Arg Trp Ser Val Glu Glu
    930                 935                 940

Val Tyr Glu Phe Ile Ala Ser Leu Gln Gly Cys Gln Glu Ile Ala Glu
945                 950                 955                 960

Glu Phe Arg Ser Gln Glu Ile Asp Gly Gln Ala Leu Leu Leu Leu Lys
                965                 970                 975

Glu Glu His Leu Met Ser Ala Met Asn Ile Lys Leu Gly Pro Ala Leu
            980                 985                 990

Lys Ile Cys Ala Lys Ile Asn Val Leu Lys Glu Thr
            995                1000
```